(12) United States Patent
Hebert

(10) Patent No.: US 7,387,796 B2
(45) Date of Patent: Jun. 17, 2008

(54) STABLE COMPOSITIONS OF S-ADENOSYL-L-METHIONINE WITH DEXTRAN

(76) Inventor: Rolland F. Hebert, 427 Bellevue Ave. E., #301, Seattle, WA (US) 98102

(*) Notice: Subject to any disclaimer, the term of this patent is extended or adjusted under 35 U.S.C. 154(b) by 631 days.

(21) Appl. No.: 10/354,363

(22) Filed: Jan. 30, 2003

(65) Prior Publication Data

US 2003/0144244 A1    Jul. 31, 2003

Related U.S. Application Data

(60) Provisional application No. 60/353,717, filed on Jan. 30, 2002.

(51) Int. Cl.
*A61K 9/14* (2006.01)
(52) U.S. Cl. .................. 424/499; 424/489; 514/59; 514/46

(58) Field of Classification Search ............... None
See application file for complete search history.

(56) References Cited

U.S. PATENT DOCUMENTS

| | | | | |
|---|---|---|---|---|
| 4,764,603 A | * | 8/1988 | Zappia et al. | 536/27.3 |
| 5,044,091 A | * | 9/1991 | Ueda et al. | 34/303 |
| 5,668,116 A | * | 9/1997 | Cullis-Hill et al. | 514/54 |
| 5,902,800 A | * | 5/1999 | Green et al. | 514/59 |
| 6,096,728 A | * | 8/2000 | Collins et al. | 514/62 |
| 6,255,295 B1 | * | 7/2001 | Henderson et al. | 514/54 |

* cited by examiner

*Primary Examiner*—Gollamudi S. Kishore

(57) ABSTRACT

Stable compositions of S-adenosyl-1-methionine with dextran are described. The compositions according to the invention are stable over time and are valuable for use as active constituents in pharmaceutical and cosmeceutical preparations.

6 Claims, No Drawings

STABLE COMPOSITIONS OF S-ADENOSYL-L-METHIONINE WITH DEXTRAN

BACKGROUND-CROSS-REFERENCES TO RELATED APPLICATIONS

This application claims the benefit of Provisional Patent Application Ser. No. 60/353,717 filed on Jan. 30, 2002.

FIELD OF THE INVENTION

The present invention relates to new stable compositions of S-adenosyl-1-methionine with dextran.

TECHNICAL FIELD

This patent relates to new compositions of S-adenosyl-1-methionine (known as SAM-e) with dextran, the processes for obtaining them and to therapeutic uses of these new compositions, more particularly, the invention relates to compositions deriving from the reaction between SAM-e, SAM-e salts and dextran, their production process and pharmaceutical compositions that contain them as active principles.

BACKGROUND OF THE INVENTION

SAM-e is a naturally occurring substance that is present in all living organisms and has a number of very important biological functions. SAM-e exists in two important diasteriomeric forms as (S,S)S-adenosyl-1-methionine and (R,S) S-adenosyl-1-methionine. Among these functions are the following: methyl group donor in transmethylation reactions (it is the sole methyl group donor in such reactions-including methylation of DNA, proteins, hormones, catechol and indoleamines and phosphatidylethanolamine to phosphatidylcholine); it is a substrate of an enzyme lyase that converts S-adenosyl-1-methionine to the molecule methylthioadenosine and homoserine; it is an aminobutyric chain donor to tRNA; it is an aminoacidic chain donor in the biosynthesis of biotin; SAM-e, after decarboxylation, is the donor of aminopropyl groups for the biosynthesis of neuroregulatory polyamines spermidine and spermine. (Zappia et al (1979) Biomedical and Pharmacological roles of Adenosylmethionine and the Central Nervous System, page 1, Pergamon Press. NY.)

SAM-e has been used clinically for more than twenty years in the treatment of liver disease (Friedel H, Goa, K. L., and Benfield P., (1989) S-Adenosyl-1-methionine: a review of its pharmacological properties and therapeutic potential in liver dysfunction and affective disorders in relation to its physiological role in cell metabolism. Drugs. 38,389-416), arthritis (Di Padova C, (1987) S-adenosyl-1-methionine in the treatment of osteoarthritis: review of the clinical studies. Am J. Med. 83, (Suppl. 5), 6-65), and depression (Kagan, B, Sultzer D. L., Rosenlicht N and Gerner R. (1990) Oral S-adenosylmethionine in depression: a randomized, double-blind, placebo-controlled trial. Am. J. Psychiatry 147, 591-595.) Alzheimer's patients have reduced cerebral spinal fluid levels of S-adenosyl-1-methionine (Bottiglieri et al, (1990) Cerebrospinal fluid S-adenosyl-1-methionine in depression and dementia: effects of treatment with parenteral and oral S-adenosyl-1-methionine. J. Neurol. Neurosurg. Psychiatry 53, 1096-1098.) In a preliminary study, SAM-e was able to produce cognitive improvement in patients with Alzheimer's disease. (Bottiglieri et al (1994) The clinical potential of admetionine (S-adenosyl-1-methionine) in neurological disorders. Drugs 48, 137-152.) SAM-e brain levels in patients with Alzheimer's disease are also severely decreased. (Morrison et al, (1996) Brain S-adenosylmethionine levels are severely decreased in Alzheimer's disease, Journal of Neurochemistry, 67, 1328-1331. Patients with Parkinson's disease have also been shown to have significantly decreased blood levels of SAM. (Cheng et al, (1997) Levels of L-methionine S-adenosyltransferase activity in erythrocytes and concentrations of S-adenosylmethionine and S-adenosylhomocysteine in whole blood of patients with Parkinson's disease. Experimental Neurology 145, 580-585.) Oral SAM-e administration to patients with and without liver disease has resulted in increases in liver glutathione levels. (Vendemiale G et al, Effect of oral S-adenosyl-1-methionine on hepatic glutathione in patients with liver disease. Scand J Gastroenterol 1989;24: 407-15. Oral administration of SAM-e to patients suffering from intrahepatic cholestasis had improvements in both the pruritus as well as the biochemical markers of cholestasis. (Giudici et al, The use of admetionine (SAM-e) in the treatment of cholestatic liver disorders. Meta-analysis of clinical trials. In: Mato et al editors. Methionine Metabolism: Molecular Mechanism and Clinical Implications. Madrid: CSIC Press; 1992 pp 67-79.) Oral SAM-e administration to patients suffering from primary fibromyalgia resulted in significant improvement after a short term trial. (Tavoni et al, Evaluation of S-adenosylmethionine in Primary Fibromyalgia. The American Journal of Medicine, Vol 83 (suppl 5A), pp 107-110, 1987.) Lee Hong Kyu disclosed in a patent application Ser. No. WO02092105 (Nov. 21, 2002) that SAM-e could be used to treat diabetes and insulin resistance. A recently published evidence report entitled "S-adenosyl-1-methionine for the treatment of depression, osteoarthritis and liver disease" provides both safety and clinical efficacy data for this important biomolecule. (Evidence Report number 64, US Department of Health and Human Services, Public Health Service, Agency for Healthcare Research and Quality. October 2002.

SAM-e is clinically useful in many apparently unrelated areas because of its important function in basic metabolic processes. One of its most striking clinical uses is in the treatment of alcoholic liver cirrhosis that, until now, remained medically untreatable. Mato et al, in 1999, demonstrated the ability of oral SAM in alcoholic liver cirrhosis to decrease the overall mortality and/or progression to liver transplant by 29% vs 12% as compared with a placebo treated group. (Mato et al, (1999) S-adenosylmethionine in alcohol liver cirrhosis: a randomized, placebo-controlled, double blind, multi-center clinical trial. Journal of Hepatology, 30, 1081-1089.) The extensive clinical use of SAM-e has proven its efficacy as well as its absence of toxicity in a number of different clinical conditions. Indeed, further basic science as well as clinical studies on this very important molecule may elucidate new uses for SAM-e in medicine.

SAM-e, however, presents certain difficult problems in terms of its stability at ambient temperature that result in degradation of the molecule to undesirable degradation products. SAM-e has therefore been the subject of numerous patents directed both towards the obtaining of new stable salts, and towards the provision of preparation processes which can be implemented on an industrial scale. There exist numerous patents disclosing many new salts of SAM-e but none discloses the use of dextran to stabilize SAM-e. U.S. Pat. No. 3,893,999, Fiecchi, Jul. 8, 1975, discloses a new salt of SAM-e made with tri-p-toluensulphonate but not the use of dextran to stabilize SAM-e. U.S. Pat. No. 3,954,726, Fiecchi, May 4, 1976, discloses double salts of SAM-e but does not disclose the use of dextran to stabilize SAM-e. U.S. Pat. No. 4,028,183, Fiecchi, Jun. 7, 1977, discloses, among others, p-toluene sulfonate as a means to stabilize the SAM-e molecule but does not disclose the use of dextran to stabilize SAM-e. U.S. Pat. No. 4,057,686, Fiecchi, Nov. 8, 1977, discloses stable salts of SAM-e but does not disclose the use of dextran to stabilize SAM-e. U.S. Pat. No. 4,465,672, Gennari, Aug. 14, 1984, discloses new SAM-e salts but does not disclose the use of dextran to stabilize SAM-e. U.S. Pat. No. 4,543,408, Gennari, Sep. 24, 1985, discloses new SAM-e salts but does not disclose the use of dextran to stabilize SAM-e. U.S. Pat. No. 4,558,122, Gennari, Dec. 10, 1985, discloses new SAM-e salts but does not disclose the use of dextran to stabilize SAM-e. U.S. Pat. No. 4,990,606, Gennari, Feb. 5, 1991, discloses new salts of SAM-e but does not disclose the use of dextran to stabilize SAM-e. U.S. Pat. No. 5,102,791, Gennari, Apr. 7, 1992, discloses, among others, a 1,4 butanedisulfonate salt of SAM-e but not the use of dextran to stabilize SAM-e. U.S. Pat. No. 5,114,931, Gennari, May 19, 1992, discloses injectable SAM-e salts but does not disclose the use of dextran to stabilize SAM-e. U.S. Pat. No. 5,128,249, Gennari, Jul. 7, 1992, discloses new SAM-e salts but does not disclose the use of dextran to stabilize SAM-e. U.S. Pat. No. 3,707,536, Haid et al, Dec. 26, 1972, discloses a new SAM-e bisulfate salt but not the use of dextran to stabilize SAM-e. U.S. Pat. No. 4,109,079 Kawahara, et al., Aug. 22, 1978, discloses new stable SAM-e salts but does not disclose the use of dextran to stabilize SAM-e. U.S. Pat. No. 4,242,505, Kawahara, et al. Dec. 30, 1980, discloses new stabilizing salts of SAM-e but does not disclose the use of dextran to stabilize SAM-e. U.S. Pat. No. 4,369,177, Kozaki et al, Jan. 18, 1983, discloses stable compositions of SAM-e and SAM-e salts using a salt of a bivalent or trivalent metal but does not disclose the use of dextran salts of SAM-e or of other SAM-e salts. U.S. Pat. No. 5,166,328 Kurobe, et al. Nov. 24, 1992 entitled "S-adenosylmethionine derivatives" does not disclose the use of dextran to stabilize SAM-e. U.S. Pat. No. 2,969,353, Shunk et al, Jan. 24, 1962, discloses a method for the preparation of SAM-e and a stable salt of SAM-e but not the use of dextran to stabilize SAM-e. U.S. Pat. No. 4,764,603, Zappia, et al. Aug. 16, 1988, discloses the use of new salts of SAM-e but does not disclose the use of dextran to stabilize SAM-e. U.S. Pat. No. 5,073,546, Zappia, et al. Dec. 17, 1991, discloses new salts of SAM-e but does not disclose the use of dextran to stabilize SAM-e. U.S. Pat. No. 6,117,849, Zimmermann, et al. Sep. 12, 2000, discloses the use of SAM-e complexed with nucleosides as HIV inhibitors but does not disclose the use of dextran to stabilize SAM-e.

Administration of new compositions of SAM-e with dextran of the present invention would have significant utility over a wide range of disorders or conditions associated with low levels of SAM-e. The new compositions of SAM-e with dextran would be more stable at room temperature over a longer period of time than current salts of SAM-e. These new compositions of SAM-e with dextran would not cause gastrointestinal upset often associated with the current SAM-e salts. In this regard, and in view of the molecular instability of SAM-e at room temperature over time, it has been suggested that a more ideal composition of SAM-e would be able to withstand the conditions of room temperature over long periods of time which would duplicate the shelf life conditions under which these new SAM-e compositions would be stored.

Dextran is used to stabilze SAM-e in its natural state or as a salt. Dextrans are macromolecules composed of glucose subunits and have been used in clinical medicine for a long time. Dextrans and SAM-e are both available commercially and are considered non-toxic.

Accordingly, there is need in the art for new, stable compositions of SAM-e as well as methods related to the use of such compositions to increase blood and other tissue and fluid levels of SAM-e and to treat conditions which result from low blood and tissue levels of SAM-e. There is also a need in the art for synthetic routes to make such new compositions. The author of this present invention fulfills these needs and provides further related advantages.

SUMMARY OF THE INVENTION

Briefly stated, the present invention discloses new, stable compositions of SAM-e with dextran, methods for the use thereof and synthetic methods for their preparation. These new compositions of SAM-e with dextran of this present invention have utility in increasing blood and other tissue or fluid levels of SAM-e, as well as treating or preventing a wide variety of conditions associated with low blood or other tissue or fluid levels of SAM-e. Thus in one embodiment, a new composition of SAM-e with dextran is administered to a warm-blooded animal in need thereof to increase SAM-e levels. In another embodiment, a new composition of SAM-e with dextran is administered to a warm blooded animal in need thereof to prevent or treat a condition associated with low levels of SAM-e. In yet a further embodiment, a new composition of SAM-e with dextran is administered to a warm blooded animal in need thereof to prevent and or treat the following conditions: aging, aging of the skin, Alzheimer's disease, arthritis, both as an antiinflammatory as well as to promote new cartilage formation and prevent cartilage destruction, nerve damage associated with HIV/AIDS, anxiety, obsessive compulsive disorder, attention deficit disorder and ADHD, sleep regulation, organ preservation for transplant industry, treatment of dyslipidemias, excess sebum production, migraines, prevention and treatment of bile dysfunction caused by pregnancy and use of contraceptive medications, cancer, depression, acute and chronic liver disease, cirrhosis of the liver, ischemic reperfusion injury of stroke as well as organ ischemic reperfusion in transplant technology, Parkinson's disease, memory disturbances, intrahepatic cholestasis, inflammation, diabetes, pain and to counteract the decrease in SAM-e caused by various cancer and immunosuppressive drugs.

DETAILED DESCRIPTION OF THE INVENTION

As mentioned above, this invention is generally directed to new compositions of SAM-e with dextran. Such new compositions of SAM-e with dextran when administered to a warm blooded animal in need thereof have utility in the prevention or treatment of conditions associated with low levels of SAM-e in warm blooded animals, including humans. The author of the present invention has surprisingly discovered that new, more stable compositions of SAM-e can be made with dextran. In addition, the author has surprisingly found that dextran is able to stabilize further SAM-e salts that were thought to be well stabilized but in fact also deteriorate over time. Thus this present invention allows for the further stabilization of all SAM-e salts to date using this relatively simple and cost effective methodology. These new salts with dextran provide steric hindrance to the unstable SAM-e molecule resulting in a much more stable molecule over time.

SAM-e is commercially available using fermentation technologies that result in SAM-e formulations varying between 60 and 80% purity. (That is, the final product contains 60-80% of the active or (S, S)-SAM-e and 20-40% of the inactive or (R, S)-SAM-e.) (Gross, A., Geresh, S., and Whitesides, Gm (1983) Appl. Biochem. Biotech. 8, 415.) Enzymatic synthetic methodologies have been reported to yield the inactive isomer in concentrations exceeding 60%. (Matos, J R, Rauschel F M, Wong, C H. S-Adenosylmethionine: Studies on Chemical and Enzymatic Synthesis. Biotechnology and Applied Biochemistry 9, 39-52 (1987). A recent U.S. patent application 20020188116 Deshpande, Pandurang Balwant; et al. Dec. 12, 2002 entitled "Chemical synthesis of S-adenosyl-L-methionine with enrichment of (S,S)-isomer." discloses methodology to synthesize SAM-e but does not disclose any methodology to stabilize the molecule once its synthesized. U.S. patent application 20020173012 Berna, Marco; et al. Nov. 21, 2002 entitled "Process for the preparation of pharmaceutically acceptable salts of (R,S)-S-adenosyl-L-methionine" disclose a process for the preparation of a relatively purified bio logically active diasteriomer (S,S) SAM-e (97%) but does not disclose stablization of the SAM-e molecule using dextran.

SAM-e (whether in its optically pure diasteriomeric form or in an enantiomeric or racemic mixture) presents certain difficult problems in terms of its stability at ambient temperature that result in degradation of the molecule to undesirable degradation products. SAM-e (and thus its diasteriomers) must be further stabilized since it exhibits intramolecular instability that causes the destabilization and breakdown of the molecule at both high as well as ambient temperatures. SAM-e has therefore been the subject of many patents directed both towards obtaining new stable salts, and towards the provision of preparation processes that can be implemented on an industrial scale. The present patent thus envisions the use of any of the salts of SAM-e already disclosed in the prior art to stabilize the diasteriomeric forms of SAM-e.

As used herein, the term "conditions" includes diseases, injuries, disorders, indications and/or afflictions that are associated with decreased levels of SAM-e. The term "treat" or "treatment" means that the symptoms associated with one or more conditions associated with low levels of SAM-e are alleviated or reduced in severity or frequency and the term "prevent" means that subsequent occurrences of such symptoms are avoided or that the frequency between such occurrences is prolonged.

Typical oral dosages for the treatment of the conditions listed above lie in the range of from 100 mg to 1600 mg or greater per day given in divided doses. IV dosages are those that have already been established for this molecule.

Owing to their simple conception and low costs, the procedures described in this invention easily lend themselves to working out methods of preparation on an industrial scale.

The following examples illustrate the synthetic process by which the new stabilized compositions of SAM-e with dextran may be made. These examples are given to illustrate the present invention, but not by way of limitation. Accordingly, the scope of this invention should be determined not by the embodiments illustrated, but rather by the appended claims and their legal equivalents.

EXAMPLE 1

Dissolve 0.5 grams of dextran in 5 ml of water and add 0.5 grams of SAM-e tosylate bisulfate. Stir solution well until completely dissolved and freeze dry. The sample was left at room temperature in the light for 12 months with no special protection. Stability of the new SAM-e salts was assessed according to the following protocol:

Isocratic high performance liquid chromatographic analysis of S-adenosylmethionine and S-adenosylhomocysteine in animal tissues: the effect of exposure to nitrous oxide. Bottiglieri, T. (1990) Biomed Chromatogr, 4(6):239-41.

| Compound | amount injected | HPLC retention time | Area of HPLC peak | conc. |
|---|---|---|---|---|
| SAM-e stand. | 10 ng/ml | 14.37 min | 189251 | 10 ng/ml |
| SAM-e tosylate-dextran | 10 ng/ml | 15.01 min | 50533 | 2.67 ng/ml |

No SAM-e breakdown products were detected, thus showing that the SAM-e remained stable for 12 months at room temperature.

EXAMPLE 2

Dissolve 0.5 grams of dextran in 5 ml of water and add 0.5 grams of (S,S)-SAM-e tosylate. Stir solution well until completely dissolved and freeze dry.

EXAMPLE 3

Dissolve 0.5 grams of dextran in 5 ml of water and add 0.5 grams of SAM-e. Stir solution well until completely dissolved and freeze dry.

EXAMPLE 4

Dissolve 0.5 grams of dextran in 5 ml of water and add 0.5 grams of SAM-e 1,4 butane disulfonate. Stir solution well until completely dissolved and freeze dry.

EXAMPLE 5

Dissolve 0.5 grams of dextran in 5 ml of water and add 0.5 grams of (S,S)-SAM-e 1,4 butane disulfonate. Stir solution well until completely dissolved and freeze dry.

EXAMPLE 6

Dissolve 0.5 grams of dextran in 5 ml of water and add 0.5 grams of (R,S)-SAM-e 1,4, butane disulfonate. Stir solution well until completely dissolved and freeze dry.

EXAMPLE 7

Dissolve 0.5 grams of dextran in 5 ml of water and add 0.5 grams of (S,S)-SAM-e. Stir solution well until completely dissolved and freeze dry.

I claim:

1. A composition useful for the treatment of conditions in warm blooded animals, including humans, that result from low cell, blood and tissue levels of S-adenosyl-L-methionine and treatable by administration of a composition comprising an effective amount of a salt of S-adenosyl-L-methionine and a dextran whereby the composition is prepared by dissolving a salt of S-adenosyl-L-methionine and a dextran in water to form a solution and drying the solution to obtain a stable dry powder.

2. The composition of claim 1 wherein the amount of dextran is present from 0.01% to 100% of the weight of the S-adenosyl-L-methionine salt.

3. The composition of claim 1 wherein the amount of dextran is present from 10% to 100% of the weight of the S-adenosyl-L-methionine salt.

4. The composition of claim 1 wherein the amount of dextran is present from 20% to 50% of the weight of the S-adenosyl-L-methionine salt.

5. A composition of claim 1 wherein an S-adenosyl-L-methionine salt is selected from the group consisting of S-adenosyl-L-methionine tosylate, S-adenosyl-L-methionine tosylate bisulfate, S-adenosyl-L-methionine 1,4-butanedisulfonate, S-adenosyl-L-methionine sulfate.

6. A composition of claim 1 wherein an S-adenosyl-L-methionine is selected from the group consisting of the optically pure diastereomer (S,S)-S-adenosyl-L-methionine or a non-racemic ratio of (S,S)-S-adenosyl-L-methionine and (R,S)-S-adenosyl-L-methionine and their pharmaceutically acceptable salts.

\* \* \* \* \*